United States Patent [19]
Hayashizaki

[11] Patent Number: 6,143,528
[45] Date of Patent: Nov. 7, 2000

[54] METHOD FOR FORMING FULL-LENGTH CDNA LIBRARIES

[75] Inventor: Yoshihide Hayashizaki, Ibaraki, Japan

[73] Assignee: The Institute of Physical and Chemical Research, Saitama, Japan

[21] Appl. No.: 09/297,383

[22] PCT Filed: Oct. 31, 1997

[86] PCT No.: PCT/JP97/03992

§ 371 Date: Jul. 16, 1999

§ 102(e) Date: Jul. 16, 1999

[87] PCT Pub. No.: WO98/20122

PCT Pub. Date: May 14, 1998

[30] Foreign Application Priority Data

Nov. 1, 1996 [JP] Japan .................................. 8-291500

[51] Int. Cl.$^7$ ..................................................... C12P 19/34
[52] U.S. Cl. ................................. 435/91.1; 435/5; 435/6; 435/91.2; 536/22.1; 536/23.1
[58] Field of Search .................................. 435/5, 6, 91.1, 435/91.2, 440; 536/22.1, 23.1

[56] References Cited

U.S. PATENT DOCUMENTS 5,891,637  4/1999  Ruppert ........................................ 435/6

OTHER PUBLICATIONS

Carninci et al. "High–efficiency full–length cDNA cloning by biotinylated CAP trapper" Genomics, vol. 37, pp. 327–336, 1996.

Edery et al., Mol. Cell. Biol. (1995), vol. 15, No. 6, p. 3363–3371 "An Efficient Strategy to Isolate Full–Length cDNAs Based on an mRNA Cap Retention Procedure (capture)".

Maruyama et al., Gene (1995), vol. 138, p. 171–174, "Oligo–capping: a simple method to replace the cap structure of eukaryotic mRNA with oligoribonucleotides".

Kato et a., Gene (1995), vol. 150, p. 243–250, "Construction of a human full–length cDNA bank".

*Primary Examiner*—Jezia Riley
*Attorney, Agent, or Firm*—Burns, Doane, Swecker & Mathis, LLP

[57] ABSTRACT

Disclose is a method for making full-length cDNA libraries, which is for making libraries of cDNAs having lengths corresponding to full lengths of mRNAs and comprises the following steps of; forming RNA-DNA hybrids by reverse transcription starting from primers using mRNAs as templates, chemically binding a tag molecule to a diol structure present in the 5' Cap ($^{Me}G_{ppp}N$) site of a mRNA which is forming a RNA-DNA hybrid, and separating RNA-DNA hybrids carrying a DNA corresponding to a full-length mRNA from the RNA-DNA hybrids formed above by using a function of the tag molecule. The present method is a method for preparing full-length cDNA libraries utilizing a method for labeling the 5' Cap site more efficiently than protein enzyme reactions, which is avoidable a decrease of a full-length cDNA synthesis efficiency caused by cleavage of mRNA, and can synthesize a full-length cDNA more efficiently.

28 Claims, 5 Drawing Sheets

METHOD FOR FORMING FULL-LENGTH CDNA LIBRARIES

TECHNICAL FIELD

The present invention relates to a method for making full-length cDNA libraries. More in detail, it relates to a method for making full-length cDNA libraries by a method for purification of full-length cDNAs utilizing chemical modification of mRNAs.

TECHNICAL BACKGROUND

Methods for synthesizing cDNAs are essential techniques for researches in the fields of medical science and biology as an indispensable method for analyzing gene transcripts. Any DNA genetic information manifests physiological activity through transcripts and a potential means for analyzing such transcripts is cDNA cloning. In cDNA syntheses according to conventional methods, clones are ultimately isolated from a cDNA library synthesized from poly A sites by using oligo dT as a primer. However, in most cases using such a method, whole structures of transcription units cannot be analyzed since the transcription units are not synthesized in their full-lengths. Therefore, when using a conventional cDNA library, it is essential for analysis of gene structures in their full-lengths to synthesize 5' upstream regions by the primer elongation method, or perform gene-walking of the 5' upstream regions by cDNA synthesis using a random primer.

However, such conventional methods for synthesizing cDNAs as described above have, for example, the following problems.

1. cDNAs covering most part of transcripts can be obtained by using a random primer. However, those cDNAs are short fragments and clones covering from the poly A site to 5' Cap site cannot be isolated.
2. Any cDNAs obtained by using oligo dT as a primer contain the 3' end. However, because the reverse transcriptase cannot reach the 5' Cap site, the 5' upstream should be further isolated and analyzed by the primer elongation method and 5' RACE or the like.
3. Efficiency of any conventional methods for isolating cDNAs in their full-lengths including those methods mentioned above is not sufficient (only 2,000,000 recombinant phages can be obtained from 100 µg of mRNA). Therefore, more efficient techniques are desired for practical purposes.

As conventional methods for synthesizing full-length cDNAs, the following methods can be mentioned;
the method utilizing a Cap binding protein of yeast or Hela cells for labeling the 5' Cap site (I. Edery et al., "An Efficient Strategy To Isolate Full-length cDNAs Based on a mRNA Cap Retention Procedure (CAPture)", MCB, 15, 3363–3371, 1995); the method where phosphates of incomplete cDNAs without 5' Cap are removed by using alkaline phosphatase and then the whole cDNAs are treated with de-capping enzyme of tobacco mosaic virus so that only the full-length cDNAs have phosphates (K. Maruyama et al., "Oligo-capping: a simple method to replace the cap structure of eukaryotic mRNAs with oligoribonucleotides", Gene, 138, 171–174, 1995., S. Kato et al., "Construction of a human full-length cDNA bank", Gene, 150, 243–250, 1995) and the like.

The reasons why efficiency of these conventional methods for synthesizing full-length cDNAs is not sufficient include, for example, the followings.

① Because the recognition of 5' Cap site depends on reactions of proteins like adenovirus Cap binding protein and the de-capping enzyme of tobacco mosaic virus, high efficiency of the selection of full-length cDNAs (RNAs) cannot be expected.

② When the first strand of cDNA is synthesized by a reverse transcriptase, the synthesized strand does not extend to the 5' Cap site.

③ There are also problems of the addition of primer sequences, synthesis efficiency of second strand, cloning efficiency of double stranded cDNA after the synthesis of the first strand, and of a host vector system for cloning.

As described above, in the production of cDNA libraries in a multi-step process, there are problems such as those mentioned as ① to ③ above.

Therefore, the first object of the present invention is to provide a novel method in which 5' Cap site can be more efficiently labeled compared with the labeling by the proteins reactions such as those by the conventional adenovirus Cap binding protein and the de-capping enzyme of tobacco mosaic virus which is directed to isolation of full-length cDNAs.

The second object of the present invention is to provide a method for making full-length cDNA libraries utilizing the novel method for labeling of the 5' Cap site. The inventors of the present invention have found a novel method for preparing a full-length cDNA libraries, and have applied for patent ahead (Japanese Patent application No. Hei 8-60459/1996).

By this method the labeling of the 5' Cap site is more efficiently performed compared to the protein enzyme reaction with the above adenovirus Cap binding protein such as Cap binding protein and Tabbaco mosaic virus, and as a result, the preparation of the full-length cDNA libraries become more easy.

However, as the inventors further studied on this method, it has been found that mRNA tends to be cleaved during a procedure of dialdehydration of a diol structure, and an efficiency of a synthesis of a full-length cDNA is decreased.

Therefore, the object of the present invention is to prepare full-length cDNA libraries utilizing a method for labeling the 5' Cap site more efficiently than protein enzyme reactions, which avoids a decrease of a full-length cDNA synthesis efficiency caused by cleavage of mRNA, and can synthesize a full-length cDNA more efficiently.

DISCLOSURE OF THE INVENTION

The present invention relates to a method for making full-length CDNA libraries which is for making libraries of cDNAs having lengths corresponding to full lengths of mRNAs and comprises the following steps of;

forming RNA-DNA hybrids by reverse transcription starting from primers such as oligo dT using the mRNAs as templates, chemically binding a tag molecule to a diol structure present in the 5' Cap ($^{7Me}G_{ppp}N$) site of a mRNA which is forming a RNA-DNA hybrid, separating RNA-DNA hybrids carrying a DNA corresponding to a full-length mRNA from the hybrids carrying a tag molecule by using a function of the tag molecule.

EMBODIMENTS FOR CARRYING OUT THE INVENTION

Figure 1:
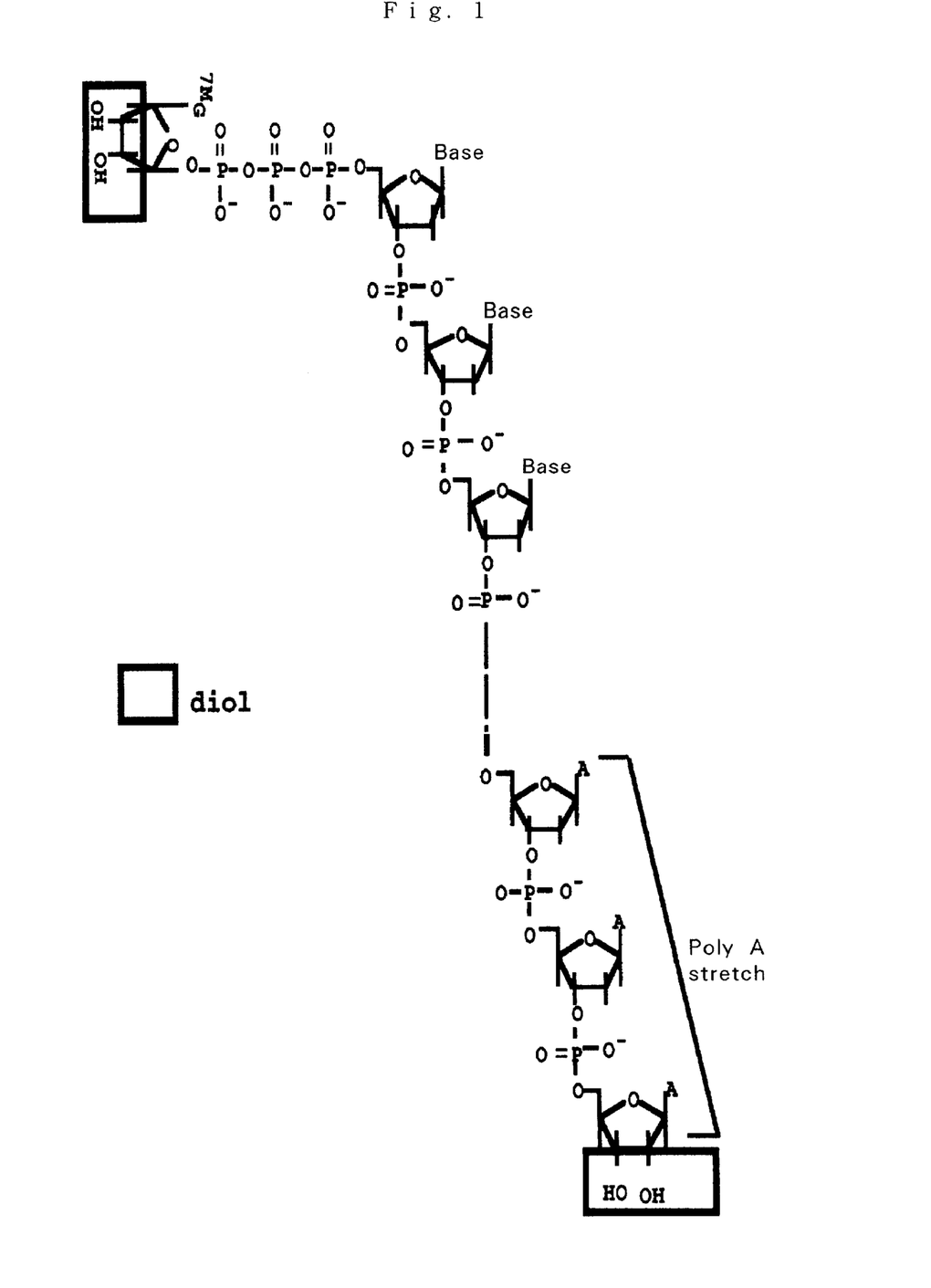
FIG. 1 shows a structure of mRNA having diol structures at both ends (the 5' Cap site and 3' site).

According to the method of the present invention, the 5' Cap site is labeled by chemical synthesis utilizing the structure specific for the 5' Cap site, a diol structure, in order to enhance the recognition of the 5' Cap site and to increase efficiency of the selection of full-length cDNAs (RNAS) (see FIG. 1).

That is, according to the method of the present invention, RNA-DNA hybrids are formed by reverse transcription using mRNAs as templates and oligo dT as a primer, and then a tag molecule is chemically bound to a diol structure present in the 5' Cap ($^{7Me}G_{ppp}$ N) site of a mRNA which is forming a RNA-DNA hybrid. This tag molecule is chemically bound to the 5' Cap site, and full-length cDNAs are synthesized by using the RNA-DNA hybrids carrying mRNAs labeled with the tag molecule.

A characteristic of the present invention is that mRNAs are labeled with the tag molecules after the formation of RNA-DNA hybrids. A hybrid structure of RNA-DNA can avoid chemical cleavage of mRNA upon aldehydration of the diol structure necessary for labeling mRNAs with the tag molecules. As a result, an efficiency of a full-length cDNA synthesis can be increased.

Figure 2:
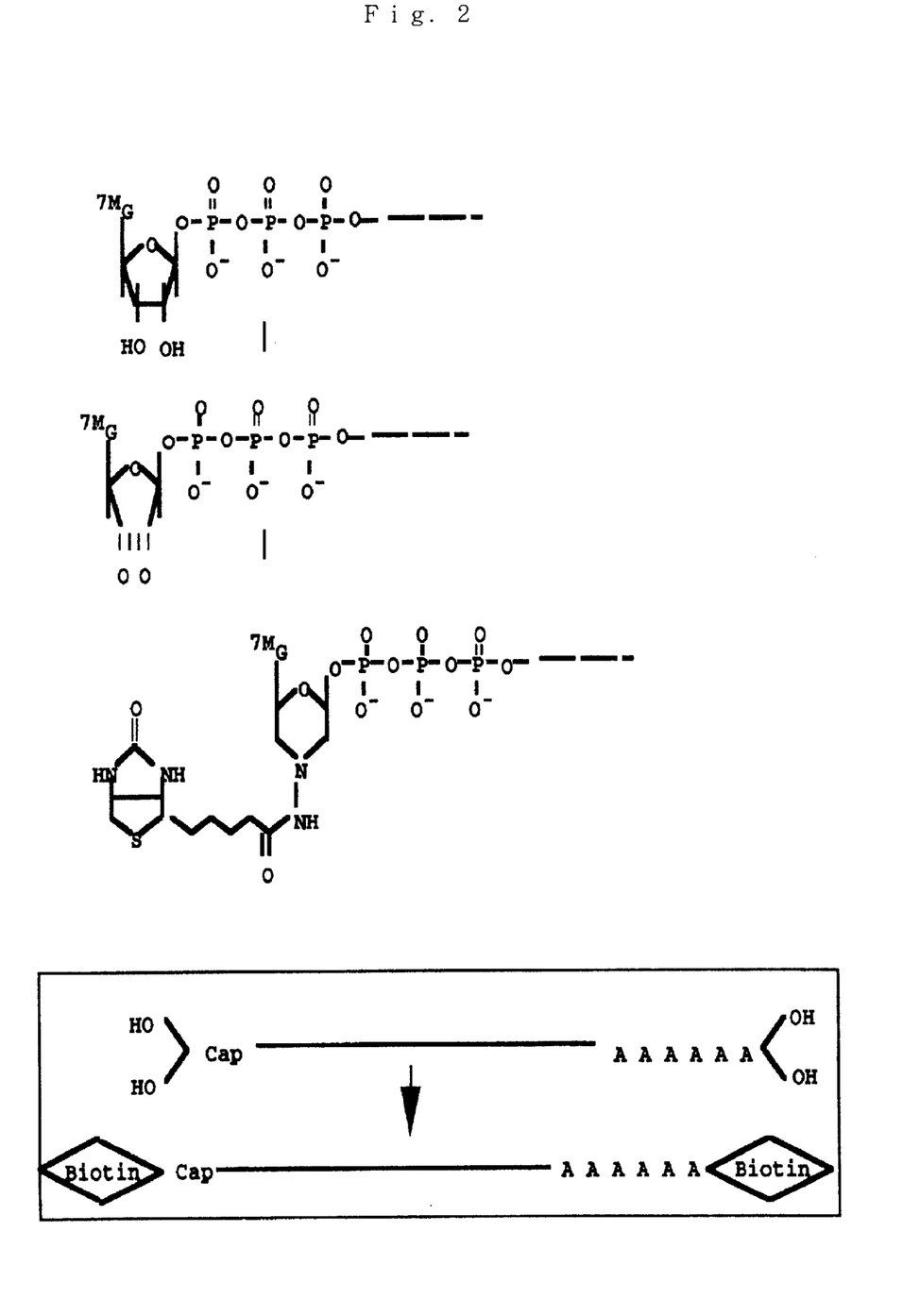
FIG. 2 shows a reaction scheme representing oxidation of the diol structure of the 5' Cap site of mRNA and addition of biotin hydrazide thereto.

The binding of the tag molecule to the 5' Cap site can be proceeded by, for example, oxidation ring-opening reaction of the 5' Cap site diol structure with an oxidizing agent such as sodium periodate ($NaIO_4$) to form a dialdehyde and subsequent reaction of the dialdehyde with a tag molecule having a hydrazine terminus, as shown in FIG. 2. Since mRNA is protected by the RNA-DNA hybrid structure in the method of the present invention, it is advantageous that oxidation cleavage of the diol structure can be done under relatively strong oxidation conditions without chemical oxidation of mRNA.

As the tag molecule having a hydrazine terminus, for example, a biotin molecule or avidin molecule having a hydrazine terminus can be mentioned. A molecule showing reaction specificity such as antigens or antibodies can also be used as the tag molecule. Specifically labeled materials used as the tag molecule are not particularly limited.

Figure 3:
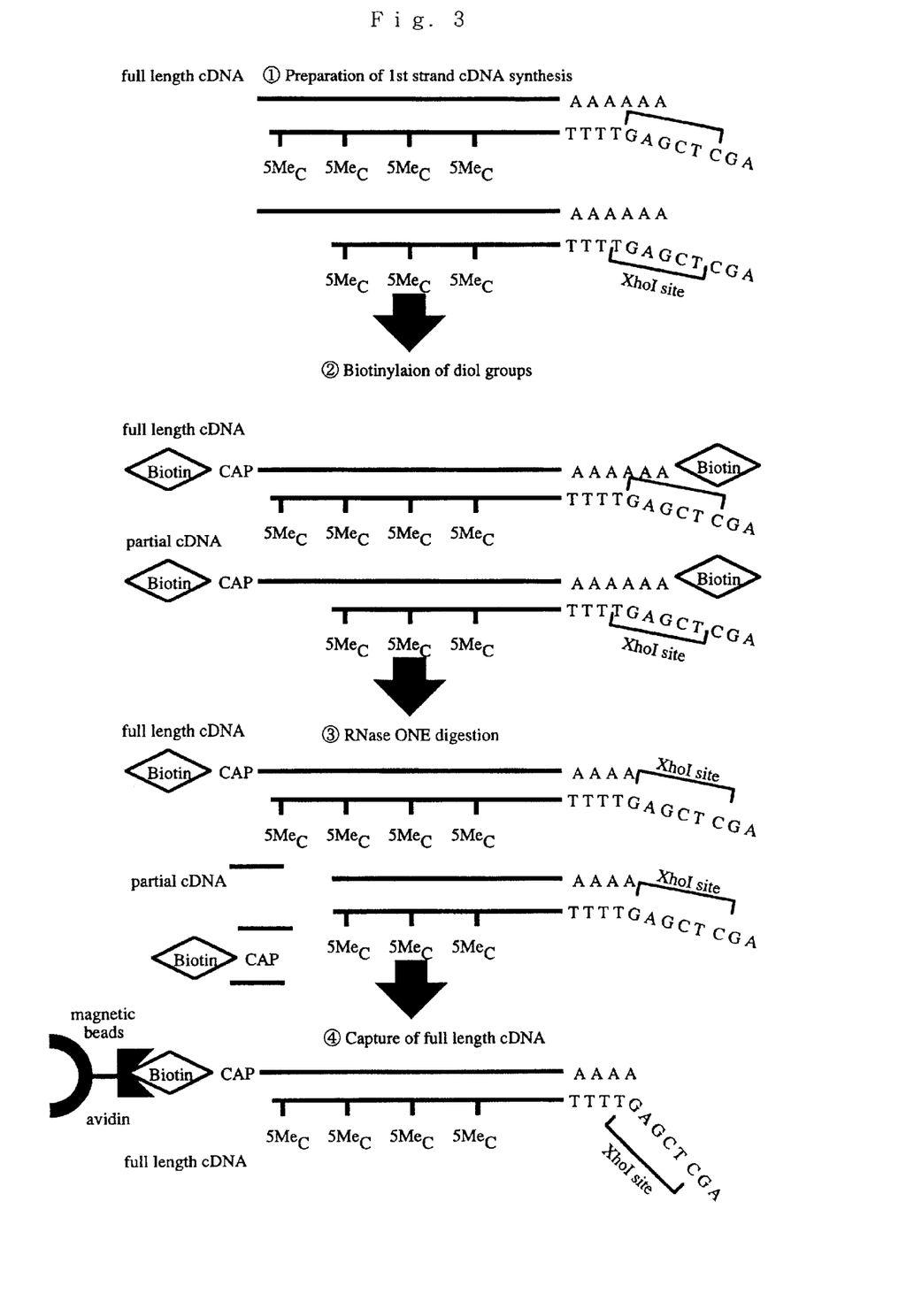
FIG. 3 is a scheme showing each step of the method for making full-length cDNAs (the first half).
Figure 4:
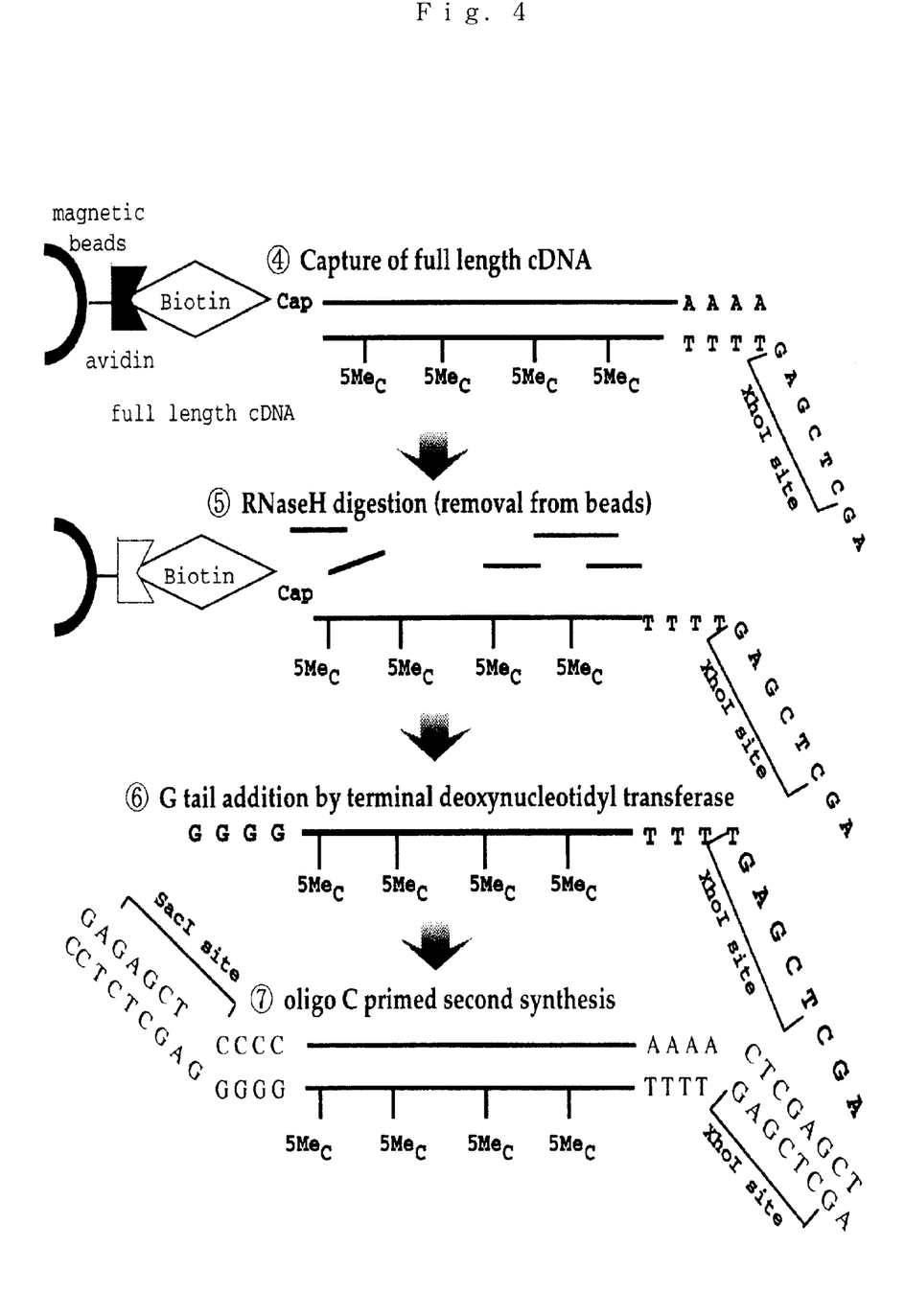
FIG. 4 is a scheme showing each step of the method for making full-length cDNAs (the latter half).

Exemplary process steps including ① synthesis of first cDNA strand to ⑦ synthesis of double-stranded full-length cDNA (tagmolecule: biotin) are shown in FIGS. 3 and 4.

① Synthesis of first strand cDNA(synthesis of a RNA-DNA hybrid)
② Biotinylation of a mRNA of the RNA-DNA hybrid
③ Ribonuclease I (RNase I) digestion
④ Capture of a full-length CDNA hybrid (with avidin beads)
⑤ RNase H digestion (removal of single-strand cDNA from the avidin beads)
⑥ G tail addition by terminal deoxynucleotidyl transferase
⑦ Preparation of second strand (double stranded full-length CDNA) primed with oligo C The RNA-DNA hybrids can be produced by reverse transcription starting from primers using the mRNAs as templates. As primers, for example, oligo dT can be used. The production of RNA-DNA hybrid by reverse transcription utilizing a primer such as oligo dT can be performed by a conventional method.

Then, the RNA-DNA hybrids are labeled with tag molecules, and then hybrids carrying a DNA corresponding to a full-length mRNA are separated from the RNA-DNA hybrids by using a function of the tag molecules.

Specifically, RNA-DNA hybrids are digested with an RNase capable of cleaving single strand RNA to cleave the single strand parts of the hybrids carrying a DNA not corresponding to a full-length mRNA. Then, those hybrids carrying a DNA corresponding to a full-length mRNA (full-length cDNAs extended to 5' Cap) are separated by utilizing a function of the tag molecules.

For example, when the tag molecule is a biotin molecule, hybrids carrying a DNA corresponding to a full-length mRNA can be separated by allowing the biotin molecules possessed by the RNA-DNA hybrids as the tag molecules to react with avidin fixed on a solid support. When the tag molecule is an avidin molecule, hybrids carrying a DNA corresponding to a full-length mRNA can be separated by allowing the avidin molecules possessed by the RNA-DNA hybrids as the tag molecules to react with biotin fixed on a solid support.

Therefore, one embodiment of the present invention relates to a method for making full-length CDNA libraries, which is for making libraries of CDNAs having lengths corresponding to full lengths of mRNAs and comprises the following steps of;

forming RNA-DNA hybrids by reverse transcription starting from primers such as oligo dT and the like using the mRNAs as templates binding a biotin molecule to a diol structure present in the 5' Cap ($^{7Me}G_{ppp}$ N) site of a mRNA which is forming a RNA-DNA hybrid, digesting RNA-DNA hybrids binding biotin molecules with an RNase capable of cleaving single strand RNA to cleave single strand RNA parts of the hybrids carrying a DNA not corresponding to a full-length mRNA to remove biotin molecules from the hybrids, and separating RNA-DNA hybrids carrying a DNA corresponding to a full-length mRNA and binding a biotin molecule by allowing them to react with avidin fixed on a solid support.

Another embodiment of the present invention relates to a method for making full-length cDNA libraries, which is for making libraries of cDNAs having lengths corresponding to full lengths of mRNAs and comprises the following steps of;

forming RNA-DNA hybrids by reverse transcription starting from primers such as oligo dT using the mRNAs as templates, binding an avidin molecule to a diol structure present in the 5' Cap ($^{7Me}G_{ppp}$ N) site of a mRNA which is forming a RNA-DNA hybrid, digesting the RNA-DNA hybrids binding avidin molecules with an RNase capable of cleaving single strand RNA to cleave the single strand RNA parts of the hybrids carrying a DNA not corresponding to a full-length mRNA to remove avidin molecules from the hybrids, and separating hybrids carrying a DNA corresponding to a full-length mRNA and binding an avidin molecule by allowing them to react with biotin fixed on a solid support.

As the RNase capable of cleaving single strand RNA, for example, ribonuclease I can be mentioned. Selection of the hybrids carrying a DNA corresponding to a full-length mRNA from the whole RNA-DNA hybrids can be performed by any means other than those using an enzyme capable of cleaving single strand RNA. That is, the method for selecting the hybrids is not particularly limited.

According to the method of the present invention, cDNAs are recovered from the separated hybrids carrying a DNA corresponding to a full-length mRNA. The recovery of the cDNAs can be performed by, for example, treating the separated hybrids carrying a DNA corresponding to a full-length mRNA with an alkaline phosphatase of tobacco mosaic virus. The recovery of the cDNAs can also be performed by treating the hybrids carrying a DNA corresponding to a full-length mRNA with an RNase capable of cleaving DNA-RNA hybrids. As such a RNase capable of cleaving DNA-RNA hybrids, for example, RNase H can be mentioned.

A full-length cDNA library can be obtained by synthesizing second cDNA strands using the recovered first cDNA strands as templates and cloning the obtained the second cDNA strands. The second cDNA strands can be synthesized by using cDNAs obtained by, for example, ligating an RNA or DNA oligomer to the 3' end of the first cDNA strands as a template and another oligomer complementary to the former ligated oligomer as a primer. Alternatively, the second cDNA strands can also be synthesized by using cDNAs obtained by ligation of poly G, poly C, poly A or poly T as a template to the 3' end of the first cDNA strands with a terminal nucleotide transferase and respectively complementary oligo C, oligo G, oligo T or oligo A as a primer.

That is, the synthesis of the second cDNA strands from the isolated full-length first cDNA can be performed by any suitable methods such as the homopolymer method using terminal deoxynucleotidyl transferase and a method comprising ligating, by an RNA ligase, a single strand primer to the 3' end of the first cDNA or 5' strand of mRNA of which 5' Cap has been removed and extending the strand with a polymerase, and therefore the method for synthesizing the second strand is not particularly limited.

According to the present invention, full-length cDNAs can be efficiently selected by chemically modification of the 5' Cap site of mRNA. This is advantageous because low background and extremely high efficiency can be obtained due to the fact that the modification for the recognition of the 5' Cap site does not depend on enzymatic reactions at all but depends on the chemical reactions utilizing the diol residue specific for the structure of the 5' Cap site of mRNA.

Further, according to the present invention, by performing chemical modification of the 5' Cap sites of mRNA after formation of RNA-DNA hybrids, degradation of chemically unstable mRNA is avoidable when the 5' Cap sites are chemically modified, and whereby decrease in efficiency of full-length cDNA synthesis is avoided. As a result, full-length cDNAs can be synthesized with higher efficiency.

In the method of the present invention, the recovery of full-length cDNAs can be performed in a solid phase system utilizing RNase I treatment and biotin-avidin reaction, which enables the production of libraries by mass productive robotics.

EXAMPLES

The method described in this example comprised the steps outlined in FIGS. 3 and 4, i.e., the following 7 steps.
① Preparation of first cDNA strand
② Biotinylation of diol groups of RNA-DNA hybrids
③ Ribonuclease I (RNase I) digestion
④ Capture of full-length cDNA hybrids (with avidin beads)
⑤ RNase H digestion (removal from the avidin beads)
⑥ G tail addition by terminal deoxynucleotidyl transferase
⑦ Preparation of second strand primed with oligo C Preparation of RNA Slices of brain tissue (0.5–1 g) were homogenized in 10 ml of a suspension and extracted with 1 ml of 2M sodium acetate (pH 4.0) and the same amount of a mixture of phenol/chloroform (volume ratio 5:1). After the extraction, the same volume of isopropanol was added to the aqueous layer to precipitate RNA. This sample was incubated on ice for an hour and centrifuged at 4000 rpm for 15 minutes with cooling to recover the precipitates. The precipitates were washed with 70% ethanol and dissolved in 8 ml of water. By adding 2 ml of 5M NaCl and 16 ml of an aqueous solution (pH 7.0) containing 1% CTAB (cetyltrimethylammonium bromide), 4M urea, and 50 mM Tris, RNA was precipitated and polysaccharides were removed (CTAB precipitate). After centrifugation at 4000 rpm for 15 minutes at room temperature, the RNA was dissolved in 4 ml of 7M guanidine-Cl. Then, two-fold amount of ethanol was added to the solution, incubated for an hour on ice and centrifuged at 4000 rpm for 15 minutes. The resulting precipitates were washed with 70% ethanol and recovered. The precipitates were again dissolved in water and purity of RNA was determined by measuring OD ratio 260/280 (>1.8) and 230/260 (<0.45).

Preparation of the first cDNA strand (FIG. 2, step ①)

Reverse transcription reaction was performed by using 15 $\mu$g of MRNA and 3000 units of Superscript II (Gibco BRL) in 165 $\mu$l of a buffer (50 mM Tris-HCl (pH8.3), 75 mM KCl, 3 mM $MgCl_2$, 10 mM DTT,) in the presence of 0.54 mM 5-methyl-dCTP, 0.54 mM dATP, 0.54 mM dTTP, 0.54 mM dGTP, 52 ng/$\mu$l BSA, 5 units of RNase inhibitor. 12.6 $\mu$l of oligonucleotide 3'NMTTTTTTTTTTTTGAGCTCTGAAT-CAAGAGAGAGAGAGAGAGAGAG5' (N: arbitrary nucleotide, M: G, A or C) including Xho I recognition site was used as a primer. At the beginning of this reaction, ¼ of the reaction solution was recovered and, to the recovered solution, 1 $\mu$l of [$\alpha$-$^{32}$P]-dGTP (3000 Ci/mmol, 10 $\mu$Ci/$\mu$l, Amersham) was added to determine synthesis yield of the first cDNA strand. 0.5 $\mu$l of the RI labeled reaction solution (20 $\mu$l) was spotted on DE-81 paper, and RI activity was measured before and after the paper was washed three times with 0.5M sodium phosphate (pH 7.0). Then, the RI labeled reaction solution and non-labeled reaction solution were mixed, added with 0.5 M EDTA 8 $\mu$l, 10 % SDS 2 $\mu$l, Proteinase K 20 $\mu$g, and heated at 45° C. for 15 minutes. The resulting mixture was then extracted with phenol/chloroform and precipitated with ethanol, and the resulting precipitate was dissolved in water treated to be RNase free (referred to "RNase free water" hereinafter) 47 $\mu$l.

Binding of biotin to diol residues of RNA (FIG. 2, step ②)

A two-step reaction, i.e., oxidation of the diol residues and subsequent coupling reaction of biotin hydrazide (Sigma) with the oxidized RNA, was performed to bind biotin to diol residues of RNA (exist at both 5' end having CAP and 3' end having poly A sequence).

First, 15 $\mu$g of RNA-first strand cDNA hybrids obtained in the reverse transcription is treated in the reaction solution of 50 $\mu$l with 6.6 mM sodium acetate buffer (pH 4.5) containing sodium periodate as an oxidizing agent. This oxidation reaction is performed on ice under light-shielding condition for 45 minutes. Then, the mixture is added with 11 $\mu$l of 5M sodium chloride, 0.5 $\mu$l of 10% SDS and the same amount of isopropanol, cooled on ice for 60 minutes and centrifuged at 15000 rpm at 4° C. for 15 minutes to afford RNA precipitates. The RNA precipitates are washed with 70% ethanol and dissolved again in 50 µl of RNase-free water. To this sample, 5 µl of 1M sodium acetate (pH 6.1), 5 µl of 10% SDS and 150 µl of 10 mM biotin hydrazide (Sigma) are added and the mixture is incubated over night at room temperature (22–26° C.). Thereafter, the sample is added with 5 µl of 5M NaCl, 75 µl of 1M sodium acetate (pH 6.1) and 2.5-fold volume of ethanol, and incubated for an hour on ice. The biotinylated RNA-DNA hybrids are precipitated again by centrifugation at 4° C. for 15 minutes. The precipitates were washed once with 70% ethanol and then with 80% ethanol. Finally, the precipitates are dissolved in RNase-free water 70 µl.

Selection of full-length CDNA with RNase I (FIG. 2, step ③)

The mRNA accompanied by cDNA not elongated completely during the reverse transcription and the biotin groups labeled at the 3' ends of mRNAs were removed by treatment of RNase I which digests single strand RNA. Specifically, 10× RNase I buffer (100 mM Tris-HCl (pH7.5), 50 mM DTA, 2 M NaOAc) 10 µl and RNase I (RNase One™: Promega) 200 units were added to 70 µl of the sample obtained by binding reaction of biotin, and single strand RNAs were digested at 37° C. for 15 minutes.

Recovery of full-length cDNA (FIG. 2, steps ④ and ⑤)

In order to avoid non-specific adsorption of cDNA to avidin coated magnetic beads, 100 µg of yeast tRNA (pretreated with DNase I) was added to 5 mg (500 µl) of magnetic beads (magnetic porous glass (MPG) particles coated with streptoavidin (CPG, NJ)), incubated on ice for an hour, and washed with a solution of 50 mM EDTA, 2MNaCl. The beads were suspended in 500 µl of a solution of 50 mM EDTA, 2 M NaCl, and to the suspension, cDNA treated with RNase I was added. The magnetic beads and the full-length CDNAS were bound by stirring at room temperature for 30 minutes. The beads captured the full-length CDNA were washed with a solution of 50 mM EDTA, 2M NaCl four times, with 0.4 % SDS, 50 µg/µl yeast tRNA once, with 10 mM NaCl, 0.2 mM EDTA, 10 mM Tris-HCl (pH 7.5), 20 % glycerol once, with a solution of 50 µg/µl yeast tRNA once, and with RNase H buffer (20 mM Tris-HCl (pH 7.5), 10 mM MgCl₂, 20 mM KCl, 0.1 mM EDTA, and 0.1 mM DTT) once. The washed beads were suspended in 100 µl of RNase H buffer, added with 3 units of RNase H, and heated at 37° C. for 30 minutes. Then 10% SDS 1 µl and 0.5 M EDTA 2 µl were added, kept it at 65° C. for 10 minutes, and the supernatant was recovered. The recovered single strand full-length cDNAs in such way were extracted with phenol/chloroform, and subjected to G25/G100 Sephadex chromatography after decreasing its volume to 100 µl or less by speed-back. Fractions with RI activity were collected in a silicon-treated micro-tube, and added with 2 µg of glycogen. The precipitate recovered by ethanol precipitation was dissolved in 30 µl of super purified water.

Oligo dG tailing of single strand cDNA (FIG. 2, steps ⑥)

The above recovered single strand cDNA 30 µl was subjected to oligo dT tailing reaction in a reaction solution of a final volume of 50 µl containing 200 MM Na cacodylate, 1 mM MgCl₂, 1 mM CoCl₂, 1 mM 2-mercaptoethanol and 100 µM dGTP (pH 6.9), using 32 units of terminal deoxynucleotidyl transferase (Takara) at 37° C. for 30 minutes. At the end of the reaction, EDTA was added to a final concentration of 50 mM and the cDNAs were extracted with phenol/chloroform, precipitated with ethanol, and dissolved in 31 µl of super purified water.

Synthesis of double-stranded CDNA (FIG. 2, step ⑦)

A synthesis of double-stranded CDNA using first strand of CDNA as a template was performed as below. To the solution containing 3 µl of the second strand low buffer (200 mM Tris-Cl, 100 mM KCl, 100 mM (NH₄)₂SO₄, 20 mM MgSO₄, 1% Triton X100, 1 mg/ml BSA, pH 8.75), 3 µl of the second strand high buffer (200 mM Tris-Cl, 600 mM KCl, 20 mM MgCl₂, pH 9.2),0.25 mM of each dCTP, dATP, dTTP, and dGTP, oligo dG-tailed single strand cDNA 31 µl, and 600 ng of the second strand primer adapter containing restriction sites of Sac I and Spe I (5'GAGAGAGAGAGAGAGAGAGAGCTCACTAGTCC-CCCCCCCCC3'), 0.25 mM dNTP's, 15 units of ExTaq polymerase (Takara Ex Taq: TaKaRa), 150 units of thermostable DNA ligase (Ampligase: Epicentre), and 3 units of thermostable RNase H (Hybridase; Epicentre) were added to afford a solution of a final volume of 60 µl.

The reaction was terminated by an addition of 0.5 M EDTA 1 µl. Further, in order to dissolve protein contents, the reaction mixture was heated in the presence of 10 % SDS 1 µl, Proteinase K 10 µg at 45° C. for 15 minutes. Finally, the double-stranded full-length cDNAs were obtained by extraction of phenol/chloroform and purification of ethanol precipitation.

Using λ ZPAII(STRATAGENE), libraries were prepared from the double stranded full-length cDNA produced by the method above. Packaging lysate for cloning was made with a conventional method using GIGAPAK Glod (SATRATAGENE). As a result, 2.5×10⁷ recombinant phages were obtained from 15 µg of mRNA. After pickup in random, with a conventional method, the cDNA was converted to plasmid clone by in vivo excison, and length of inserted cDNAs in the libraries was measured with agarose gel electrophoresis and tallied. The result is shown in Table 1.

From a comparison of the result shown in Table 1 and 2 shown below (Result of evaluation of the libraries obtained from the method disclosed in Japanese Patent Application No. Hie 8-60459/1998, and the method of a Reference Example 1 described in the followings), it is shown that an average length of cDNA obtained in the method of the present invention is significantly increased compared to that of the previous method, and also a number of clones having fragment sizes over 5000 is doubled or more. These results show that the method of the present invention is far superior from the viewpoint of obtaining longer and full-length cDNA.

TABLE 1

An average induced length: 1810 bp

| Fragment size | Number of clones | percentage |
|---|---|---|
| No induction | 70 | |
| 0~500 | 8 | 0.8 |
| ~1000 | 289 | 29.7 |
| ~1500 | 232 | 23.8 |
| ~2000 | 152 | 15.6 |
| ~2500 | 110 | 11.3 |
| ~3000 | 41 | 4.2 |
| ~3500 | 37 | 3.8 |
| ~4000 | 34 | 3.5 |
| ~4500 | 14 | 1.4 |
| ~5000 | 18 | 1.8 |
| ~5500 | 13 | 1.3 |
| ~6000 | 6 | 0.6 |
| ~6500 | 8 | 0.8 |
| ~7000 | 6 | 0.6 |
| >7000 | 6 | 0.6 |
| Total | 1044 | 100.0 |

TABLE 2

An average inserted length: 1602 bp

| Fragment size | Number of clones | percentage |
|---|---|---|
| No insertion | 93 | |
| 0~500 | 7 | 0.8 |
| ~1000 | 295 | 33.0 |
| ~1500 | 240 | 26.8 |
| ~2000 | 141 | 15.8 |
| ~2500 | 81 | 9.1 |
| ~3000 | 45 | 5.0 |
| ~3500 | 23 | 2.6 |
| ~4000 | 25 | 2.8 |
| ~4500 | 11 | 1.2 |
| ~5000 | 14 | 1.6 |
| ~5500 | 5 | 0.6 |
| ~6000 | 2 | 0.2 |
| ~6500 | 1 | 0.1 |
| ~7000 | 2 | 0.2 |
| >7000 | 2 | 0.2 |
| Total | 987 | 100.0 |

Reference Example 1

With a library of double stranded full-length cDNAs obtained by the method of Japanese Patent Application No. Hei 8-60459/1998 (the previous method) using mRNA obtained by the same procedure as those of Example 1, lengths of inserted cDNAs were measured and tallied. The results are shown in Table 2 above. Further, double stranded full-length cDNAs were prepared by a method described below.

Synthesis of mRNA-cDNA hybrids

Reverse transcription reaction was performed by using 10 µl of mRNA and 2000 units of Superscript II (Gibco BRL) in 100 µl of a buffer (50 mM Tris-HCl, 75 mM KCl, 3 mM MgCl$_2$, 10 mM DTT) in the presence of 0.5 mM 5-methyl-dCTP, 1 mM dATP, 1 mM dTTP and 1 mM dGTP. 5 µg of oligonucleotide 3'NMTTTTTTTTTTTTGAGCTCTGAAT-CAAGAGAGAGAGAGAGAGAGAG5' (N: arbitrary nucleotide, M: G, A or C) was used as a primer. The reaction was performed at 42° C. for 45 minutes, then the reaction solution was incubated at 50° C. for 20 minutes to synthesize mRNA-cDNA hybrids.

After the reaction above, the sample was put on ice immediately. Then 4 µl of 0.5 M EDTA, 8 µl of 5M NaCl and 163 µl of H$_2$O were added to the sample to make its final volume of 200 µl. After stirring and brief centrifugation, the mixture was put into an Eppendorf tube, and added with 100 µl of phenol/Tris and 100 µl of chloroform. The mixture was stirred, and after cooling on ice for 2 minutes, centrifuged at 15,000 rpm for 3 minutes. After removing an aqueous layer, the resulting mixture was put into a new Eppendorf tube. Subsequently, 100 µl of chloroform was added, and the mixture was stirred and centrifuged at 15,000 rpm for 3 minutes after cooling on ice for 2 minutes. After removal of an aqueous phase, the remains were put into a new Eppendorf tube. To the tube, 500 µl of 100 % ethanol was added, stirred, and cooled at least 10 minutes on ice. Then the tube was centrifuged at 16000 rpm for at least 10 minutes. Subsequently, the cDNA was washed with 70% and 80% ethanol twice. It was confirmed by measurement of the supernatant with a Geiger counter that most of radioactive nucleotides were removed. The produced pellet was suspended in 47 µl of ethanol.

At the beginning of this reaction, 20 µl of the reaction solution was taken and, to the solution, 1 µl of [α-$^{32}$P]-dGTP (3000 Ci/mmol, 10 µCi/gµ, Amersham) was added to determine synthesis yield of the first CDNA strand. 0.5 µl of the RI labeled reaction solution (20 µl) was spotted on DE-81 paper, and RI activity was measured before and after the paper was washed three times with 0.5M sodium phosphate (pH 7.0).

Binding of biotin to diol residues of RNA

A two-step reaction, i.e., oxidation of the diol residues and subsequent coupling reaction of biotin hydrazide (Sigma) with the oxidized RNA, was performed to bind biotin to diol residues of mRNA (CAP and 3' end of RNA) of mRNA-cDNA hybrids.

To the mRNA-cDNA hybrids suspended in 47 µl of water prepared in the above procedure, 3.3 µl of 66 mM sodium acetate buffer (pH 4.5) and 1.290 µl of 0.2 M sodium periodate as an oxidizing agent were added and stirred. The oxidation reaction was performed on ice under light-shielding condition for 45 minutes.

Then, to the mixture, 11 µl of 5M sodium chloride, 0.5 µl of 10% SDS and 6 µl of isopropanol were added, incubated on ice for 30 minutes and centrifuged for 10–20 minutes. During these procedures, 10 mM biotin hydrazide (long-arm) solution (3.7 mg/1 ml) was prepared.

The precipitates recovered in the centrifugation were washed with 200 µl of 80% ethanol and dissolved again in 50 µl of water. To this sample, 5 µl of 1M sodium acetate (pH 6.1), 5 µl of 10% SDS and 150 µl of 10 mM biotin hydrazide (an aqueous solution) were added. The mixture was incubated on ice for an hour, centrifuged for 20 minutes, and washed twice with 70% ethanol. Finally, the mixture was suspended in a suitable amount of water which is then used as a material of the next step.

RNase protection of full-length cDNA mRNAs paired with cDNAs which had not been completely extended by the reverse transcription and the biotin residues labeled at the 3' end of mRNAs were removed by treatment with RNase ONET™ (Promega) capable of digesting single strand RNAs at any nucleotide site. More specifically, when the mRNA-cDNA hybrids were synthesized, 20 µl of an RI labeled reaction solution and 80 µl of an unlabeled reaction solution were pooled together, and the sample was incubated at 30° C. for 30 minutes with 40 µl of an RNase I buffer, 355 µl of water and 50 units of RNase I.

Recovery of full-length cDNA

In order to avoid non-specific adsorption to avidin coated magnetic beads, 2.5 mg of yeast tRNA (pre-treated with DNase I) was added to the beads, and the mixture was made 500 µl in volume and incubated on ice for an hour. The cDNAs treated with RNase I were added to the above pre-treated beads and were incubated in a buffer containing 0.25 M EDTA and 0.5 M NaCl (pH 8.0) at room temperature for 15 minutes with occasional shaking so that the magnetic beads should not precipitate. Then, the beads were washed with 0.5 MEDTA (pH 8.0) four times, with 0.4% SDS once and with nuclease-free water three times. After the sample was treated with 2 units of RNase H in 100 µl of an RNase H buffer at 37° C. for 30 minutes, full-length cDNAs were removed from the beads by incubation of the beads with 0.1% SDS. cDNAs which had not been separated due to incomplete treatment with RNase H could be recovered by alkaline hydrolysis in a Tris-formate buffer (pH 9.0) at 65° C. for 10 minutes. The recovered full-length single strand cDNAs were extracted once with phenol/chloroform and subjected to G25/G50 Sephadex chromatography. Fractions showing RI activity were collected in an Eppendorf tube having a silicon coated surface and the sample volume was decreased to 10 µl by vacuum suction.

Oligo dG tailing of single strand cDNA

In order to add oligo dG to the recovered single strand cDNAs, reaction using 32 units of terminal deoxynucleotidyl transferase (Takara) was conducted in 50 μl of a buffer containing 200 mM Na cacodylate, 1 mM $MgCl_2$, 1 mM $CoCl_2$, 1 mM 2-mercaptoethanol and 100 μM dGTP (pH 6.9) at 37° C. for 30 minutes. EDTA was added to a final concentration of 50 mM and the cDNAs were extracted with phenol/chloroform and subjected to G25/G100 chromatography. The volume of the recovered dG-tailed CDNA was decreased to 30 μl by vacuum suction.

Synthesis of double-stranded cDNA

To the solution containing oligo dG-tailed single strand cDNA, 6 μl of a second strand low buffer (200 mM Tris-Cl, 100 mM KCl, 100 mM $(NH_4)_2SO_4$, 20 mM $MgSO_4$, 1% Triton X100, 1 mg/ml BSA, pH 8.75), 3 μl of a second strand high buffer (200 mM Tris-Cl, 600 mM KCl, 20 mM $MgCl_2$, pH 9.2), 600 ng of a second strand primer adapter with a sequence recognizable by restriction enzymes Sac I and Spe I (5'GAGAGAGAGAGAGAGAGAGAGCTCACTAGTCC-CCCCCCCCC3'), 0.25 mM dNTP's, 15 units of ExTaq polymerase (Takara), 150 units of Ampligase, thermostable DNA ligase (Epicentre), 3 units of hybridase and thermostable RNaseH (Epicentre) were added to give a final volume of 60 μl. Temperature of the reaction mixture was controlled by a thermocycler at 55° C. for 5 minutes, then gradually lowered from 55° C. to 35° C. at a rate of 0.3° C./minute, kept at 35° C. for 15 minutes and at 72° C. for 15 minutes for the reaction. Annealing/extension were repeated by incubating the sample at 35° C. for one hour and at 65° C. for 30 minutes. Finally, the sample was extracted with phenol/chloroform, and double stranded cDNAs were recovered by ethanol precipitation. With the obtained double stranded cDNAs, lengths of inserted cDNAs were measured in the same method as that of Example 1.

Example 2

Figure 5:
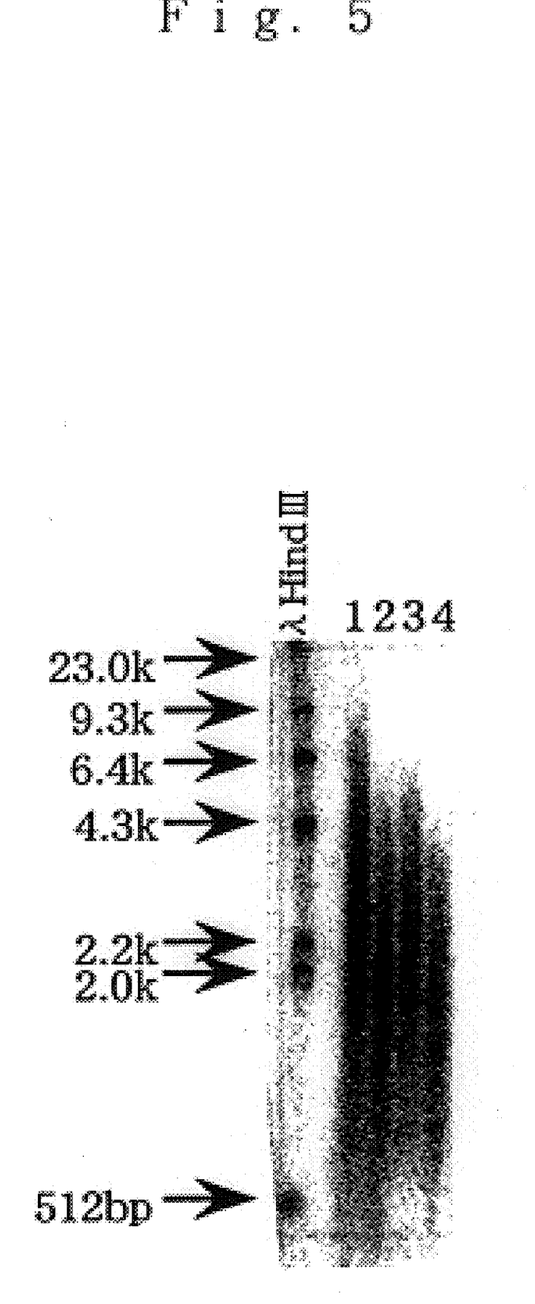
FIG. 5 is a photograph showing an autoradiography obtained in Example 2 after an electrophoresis.

In the present Example, in order to demonstrate that chemical cleavage of mRNA occurring during aldehydration of the diol structure necessary for labeling mRNAs with tag molecules can be avoided by RNA-DNA hybrid structure, and as a result a synthesis efficiency of full-length cDNAs can be increased, results of autoradiograpy after denatured agarose gel electrophoresis of RNA-DNA hybrid obtained in 4 different kinds of processes as shown lanes 1–4 are shown in FIG. 5 (size markers are λ Hind III).

In the results shown in FIG. 5, comparing lane 1 to lane 2, long chain products are observed more in lane 1 than those in lane 2 are. It is understood that chemical cleavage of mRNA is inhibited by RNA-DNA hybrid structure formed by cDNA synthesis made in advance. Further, comparing lane 3 to lane 4, long chain products are observed more in lane 3 than those in lane 4 are. It is understood that chemical cleavage of mRNA is inhibited by RNA-DNA hybrid structure formed by cDNA synthesis made in advance.

[Lane 1] 10 μg mRNA→① synthesis of cDNA(labeled with [-$^{32}$P] dGTP)→② biotinylation→③ capture of only full-length cDNA using avidin beads denatured agarose gel electrophoresis

[Lane 2] 10 μg mRNA→② biotinylation→① synthesis of cDNA(labeled with [-$^{32}$P] dGTP)→③ capture of only full-length cDNA using avidin beads→denatured agarose gel electrophoresis

[Lane 3] 5 μg mRNA→① synthesis of CDNA(labeled with [-$^{32}$P] dGTP)→② biotinylation→denatured agarose gel electrophoresis

[Lane 4] 5 μg MRNA→② biotinylation→① synthesis of CDNA (labeled with [-$^{32}$P] dGTP)→denatured agarose gel electrophoresis

[Lane 1]

① Synthesis of the first strand cDNA: labeling with [-$^{32}$P] dGTp

| [1] | mRNA | 10 μg |
| --- | --- | --- |
|  | Primer | 8.4 μg |
|  | DW | An amount to give a final volume of 100 μl when [1] and [2] were added |
| [2] | 5 × first strand bufer (GIBCO BRL) | 18.18 μl |
|  | 0.1M DTT | 9.09 μl |
|  | 10 mM dNTP mix* | 5.91 μl |
|  | BSA (2.5 μg/μg) | 2.27 μl |
|  | [$^{32}$P] dGTP (10 μCi/μl) | 1.0 μl |
|  | RNase inhibitor (25000 U/ml) | 0.91 μl |
|  | Superscript ™ II RNase H-reverse transcriptase (200 U/μl) (GIBCO BRL) | 10.0 μl |
|  | Total | 100 μl |

*Consisting of 10 mM each of 5-methyl-dCTP, dATP, dTTP, dGTP.

[1] was heat-denatured at 65° C. for 10 minutes, and immediately put on ice.

Then, [1] and [2] were incubated at an annealing temperature of 35° C. for one minute, and mixed. After the reaction, CDNA was extracted with phenol/chloroform, precipitated with ethanol, and dissolved in 47 μl of RNase free water.

② Biotinylation of diol group of RNA (a) oxidation of diol group

| (1) Sample obtained above | 47 μl |
| --- | --- |
| 1M NaOAc (pH 4.5) | 3.3 μl |
| 0.2M $NaIO_4$ | 1.29 μl |

The above were left in dark on ice for 45 minutes.

| (2) 5M NaCl | 11 μl |
| --- | --- |
| 10% SDS | 0.5 μl |
| isopropanol | 61 μl |

The above were added, and after the mixture was incubated at 4° C. for 30 minutes, precipitates obtained by centrifugation at 15000 rpm for 15 minutes(4° C.) was rinsed with 70% ethanol twice, and dissolved in 50 μl of RNase free water.

(b) Biotinylation

| (1) 1M NaOAc (pH 6.1) | 5 μl |
| --- | --- |
| 10% SDS | 5 μl |
| 10 mM biotin hydrazide (Sigma) | 150 μl |

The above were added, and reacted over night at room temperature.

| | |
|---|---|
| (2) 1M NaOAc (pH 6.1) | 75 µl |
| 5M NaCl | 5 µl |
| Ethanol | 750 µl |

The above were added, put on ice for an hour, centrifuged at 15000 rpm for 15 minutes (4° C.), and the resulting precipitate was rinsed with 70% ethanol twice. Finally, cDNAs were dissolved in 70 µl of RNase free water.

③ Capture of full-length cDNA using streptoavidin beads (a) Selection of full-length cDNA

| | |
|---|---|
| The sample obtained above | 70 µl |
| 10 × RNase I buffer | 10 µl |
| RNase One ™ (Promega) (10 U/µl) | 20 µl |
| Total | 100 µl |

The above were incubated at 37° C. for 15 minutes.

(b) Capture of full-length cDNA with streptoavidin beads (1) Binding of streptoavidin beads (MPG) and biotinylated RNA-DNA

| | |
|---|---|
| Streptoavidin coated magnetic porous glass (MPG) (CPG, NJ) (1 mg/ml) | 500 µl |
| Biotinylated RNA-first strand cDNA | 100 µl |

The above were stirred at room temperature for 30 minutes.

(2) Washing of MPG

[1] Washed with a solution of 50 mM EDTA and 2 M NaCl four times,
[2] a solution of 0.4% SDS and 50 µg/µl yeast tRNA once,
[3] 10 mM NaCl, 0.2 mM EDTA, 10 mM Tris-HCl (pH 7.5), and 20% glycerol once,
[4] an aqueous solution of 50 µg/µl of yeast tRNA solution once,
[5] RNase H buffer (20 mM Tris-HCl (pH7.5), 10 mM mgCl$_2$, 20 mM KCl, 0.1 mM EDTA, and 0.1 mM DTT) once.

(3) Recovery of full-length CDNA with RNase H

| | |
|---|---|
| [1] RNase H buffer | 100 µl |
| RNase H | 3 units |

The above were added to the washed MPG and heated at 37° C. for 30 minutes.

| | |
|---|---|
| [2] 10% SDS | 1 µl |
| 0.5M EDTA | 2 µl |

The above were added, heated for 10 minutes at 65° C. and the supernatant was recovered.

(c) CDNA in the supernatant was extracted with phenol/chloroform treatment, and purified by ethanol precipitation.

[Lane2]

① Biotinylation of diol group of RN A (a) Oxidation of diol group

| | |
|---|---|
| (1) mRNA (10 µg) | 47 µl |
| 1M NaOAc (pH 4.5) | 3.3 µl |
| 0.2M NaIO$_4$ | 1.29 µl |

The above were left in dark on ice for 45 minutes.

| | |
|---|---|
| (2) 5M NaCl | 11 µl |
| 10% SDS | 0.5 µl |
| Isopropanol | 61 µl |

The above were added, incubated for 30 minutes at 4° C., centrifuged at 15000 rpm for 15 minutes (4° C.), and the obtained precipitate was rinsed with 70% ethanol twice and dissolved in 50 µl of RNase free water.

(b) Biotinylation

| | |
|---|---|
| (1) 1M NaOAc (pH 6.1) | 5 µl |
| 10% SDS | 5 µl |
| 10 mM biotin hydrazide (Sigma) | 150 µl |

The above were added and reacted over night at room temperature.

| | |
|---|---|
| (2) 1M NaOAc (pH 6.1) | 75 µl |
| 5M NaCl | 5 µl |
| Ethanol | 750 µl |

The above were added, put on ice for an hour, centrifuged at 15000 rpm for 15 minutes (4° C.), and the resulting precipitate was rinsed twice with 70% ethanol. Finally, the precipitate was dissolved in RNase free water.

② Synthesis of first strand of cDNA: labeled with [-$^{32}$P] dGTP

| | |
|---|---|
| [1] Biotinylated mRNA | 5 µg |
| Primer | 8.4 µg |
| DW | An amount to give a final volume of 100 µl when [1] and [2] were added |
| [2] 5 × first strand bufer (GIBCO BRL) | 18.18 µl |
| 0.1M DTT | 9.09 µl |
| 10 mM dNTP mix* | 5.91 µl |
| BSA (2.5 µg/µg) | 2.27 µl |
| [—$^{32}$P] dGTP (10 µCi/µl) | 1.0 µl |
| RNase inhibitor (25000 U/ml) | 0.91 µl |
| Superscript ™ II RNase H-reverse transcriptase (200 U/µl) (GIBCO BRL) | 10.0 µl |
| Total | 100 µl |

*Consisting of 10 mM each of 5-metyl-dCTP, dATP, dTTP, dGTP.

[1] was heat-denatured at 65° C. for 10 minutes, and immediately put on ice.

Then, [1] and [2] were incubated at annealing temperature of 35° C. for one minute, and mixed.

③ Capture of full-length CDNA using streptoavidin beads
(a) Selection of full-length cDNA

| | |
|---|---|
| The sample obtained above | 100 µl |
| 10 × RNase I buffer | 50 µl |
| RNase One ™ (Promega) (10 U/µl) | 5 µl |
| DW | 345 µl |
| Total | 100 µl |

The above were incubated at 30° C. for 30 minutes.
(b) Capture of full-length cDNA with streptoavidin beads
(1) Binding of streptoavidin beads (MPG) and biotinylated RNA-DNA

| | |
|---|---|
| Streptoavidin coated magnetic porous glass (MPG) (CPG, NJ) (1 mg/ml) | 500 µl |
| The sample obtained above | 500 µl |

The above were stirred at room temperature for 30 minutes.
(2) washing of MPG
[1] Washed with a solution of 50 mM EDTA and 2 M NaCl four times,
[2] a solution of 0.4% SDS and 50 µg/µl yeast tRNA once,
[3] 10 mM NaCl, 0.2 mM EDTA, 10 mM Tris-HCl (pH 7.5), and 20% glycerol once,
[4] an aqueous solution of 50 µg/µl of yeast tRNA once,
[5] RNase H buffer (20 mM Tris-HCl (pH7.5), 10 mM MgCl$_2$, 20 mM KCl, 0.1 mM EDTA, and 0.1 mM DTT) once.
(3) Recovery of full-length cDNA with RNase H

| | | |
|---|---|---|
| [1] | RNase H buffer | 100 µl |
| | RNase H | 3 units |

The above were added to the washed MPG and heated at 37° C. for 30 minutes.

| | | |
|---|---|---|
| [2] | 10% SDS | 1 µl |
| | 0.5M EDTA | 2 µl |

The above were added, heated for 10 minutes at 65° C., and the supernatant was recovered.
(c) cDNA in the supernatant was extracted with phenol/chloroform treatment, and purified by ethanol precipitation.
[Lane 3]
① Synthesis of the first strand CDNA: labeling with [-$^{32}$P] dGTP

| | | |
|---|---|---|
| [1] | mRNA | 5 µg |
| | Primer | 8.4 µg |
| | DW | An amount to give a final volume of 100 µl when [1] and [2] were added |
| [2] | 5 × first strand buffer (GIBCO BRL) | 18.18 µl |
| | 0.1M DTT | 9.09 µl |
| | 10 mM dNTP mix* | 5.91 µl |
| | BSA (2.5 µg/µg) | 2.27 µl |
| | [-$^{32}$P] dGTP (10 µCi/µl) | 1.0 µl |

-continued

| | |
|---|---|
| RNase inhibitor (25000 U/ml) | 0.91 µl |
| Superscript ™ II RNase H-reverse transcriptase (200 U/µl) (GIBCO BRL) | 10.0 µl |
| Total | 100 µl |

*Consisting of 10 mM each of 5-methyl-dCTP, dATP, dTTP, dGTP

[1] was heat-denatured at 65° C. for 10 minutes, and immediately put on ice.
Then, [1] and [2] were incubated at annealing temperature of 35° C. for one minute, and mixed. After the reaction, cDNA was extracted with phenol/chloroform treatment, precipitated with ethanol, and dissolved in 47 µl of RNase free water.
② Biotinylation of diol group of RNA
(a) Oxidation of diol group

| | | |
|---|---|---|
| (1) | The sample obtained above | 47 µl |
| | 1M NaOAc (pH 4.5) | 3.3 µl |
| | 0.2M NaIO$_4$ | 1.29 µl |

The above were left in dark on ice for 45 minutes.

| | | |
|---|---|---|
| (2) | 5M NaCl | 11 µl |
| | 10% SDS | 0.5 µl |
| | Isopropanol | 61 µl |

The above were added, and after the mixture was incubated at 4° C. for 30 minutes, the precipitate obtained in centrifugation at 15000 rpm for 15 minutes(4° C.) was rinsed with 70% ethanol twice, and dissolved in 50 µl of RNase free water.
(b) Biotinylation

| | | |
|---|---|---|
| (1) | 1M NaOAc (pH 6.1) | 5 µl |
| | 10% SDS | 5 µl |
| | 10 mM biotin hydrazide (Sigma) | 150 µl |

The above were added, and reacted over night at room temperature.

| | | |
|---|---|---|
| (2) | 1M NaOAc (pH 6.1) | 75 µl |
| | 5M NaCl | 5 µl |
| | Ethanol | 750 µl |

The above were added, put on ice for an hour, centrifuged at 15000 rpm for 15 minutes (4° C.), and the resulting precipitate was rinsed with 70% ethanol twice. Finally, the cDNAs were dissolved in 70 µl of RNase free water.
③ Capture of full-length cDNA using streptoavidin beads
(a) Selection of full-length cDNA

| | |
|---|---|
| The sample obtained above | 70 µl |
| 10 × RNase I buffer | 10 µl |

-continued

| | |
|---|---|
| RNase One ™ (Promega) (10 U/µl) | 20 µl |
| Total | 100 µl |

The above were incubated at 37° C. for 15 minutes.

(b) Capture of full-length cDNA with streptoavidin beads (1) Binding of Streptoavidin beads (MPG) and Biotinylated RNA-DNA

| | |
|---|---|
| Streptoavidin coated magnetic porous glass (MPG) (CPG, NJ) (1 mg/ml) | 500 µl |
| Biotinylated RNA-first strand cDNA | 100 µl |

The above were stirred at room temperature for 30 minutes.

(2) Washing of MPG

[1] Washed with a solution of 50 mM EDTA and 2 M NaCl four times,
[2] a solution of 0.4% SDS and 50 µg/µl yeast tRNA once,
[3] 10 mM NaCl, 0.2 mM EDTA, 10 mM Tris-HCl(pH 7.5), and 20% glycerol once,
[4] an aqueous solution of 50 µg/µl of yeast tRNA once,
[5] RNase H buffer (20 mM Tris-HCl (pH7.5), 10 mM $MgCl_2$, 20 mM KCl, 0.1 mM EDTA, and 0.1 mM DTT) once.

(3) Recover of full-length cDNA with RNase H

| | |
|---|---|
| [1] RNase H buffer | 100 µl |
| RNase H | 3 units |

The above were added to washed MPG and heated at 37° C. for 30 minutes.

| | |
|---|---|
| [2] 10% SDS | 1 µl |
| 0.5M EDTA | 2 µl |

The above were added, heated for 10 minutes at 65° C., and the supernatant was recovered.

(c) cDNA in the supernatant was extracted with phenol/chloroform treatment, and purified by ethanol precipitation.

[Lane 4]

① Biotinylation of diol group of RNA (a) Oxidation of diol group

| | |
|---|---|
| (1) mRNA (5 µg) | 47 µl |
| 1M NaOAc (pH 4.5) | 3.3 µl |
| 0.2M $NaIO_4$ | 1.29 µl |

The above were left in dark on ice for 45 minutes.

| | |
|---|---|
| (2) 5M NaCl | 11 µl |
| 10% SDS | 0.5 µl |
| isopropanol | 61 µl |

The above were added, incubated for 30 minutes at 4° C., centrifuged at 15000 rpm for 15 minutes (4° C.), and the obtained precipitate was rinsed twice with 70% ethanol and dissolved in 50 µl of RNase free water.

(b) Biotinylation

| | |
|---|---|
| [1] 1M NaOAc (pH 6.1) | 5 µl |
| 10% SDS | 5 µl |
| 10 mM biotin hydrazide (Sigma) | 150 µl |

The above were added and reacted over night at room temperature.

| | |
|---|---|
| [2] 1M NaOAc (pH 6.1) | 75 µl |
| 5M NaCl | 5 µl |
| Ethanol | 750 µl |

The above were added, put on ice for an hour, centrifuged at 15000 rpm for 15 minutes (4° C.), and the resulting precipitate was rinsed twice with 70% ethanol. Finally, the precipitate was dissolved in RNase free water.

② Synthesis of first strand of cDNA: labeled with [-$^{32}$P]dGTP

| | |
|---|---|
| [1] Biotinylated mRNA | 5 µg |
| Primer | 8.4 µg |
| DW | An amount to give a final volume of 100 µl when [1] and [2] were added |
| [2] 5 × first strand buffer (GIBCO BRL) | 18.18 µl |
| 0.1M DTT | 9.09 µl |
| 10 mM dNTP mix* | 5.91 µl |
| BSA (2.5 µg/µg) | 2.27 µl |
| [-$^{32}$P] dGTP (10 µCi/µl) | 1.0 µl |
| RNase inhibitor (25000 U/ml) | 1.0 µl |
| Superscript ™ II RNase H-reverse trancriptase (200 U/µl) (GIBCO BRL) | 10.0 µl |
| Total | 100 µl |

*Consisting of 10 mM each of 5-methyl-dCTP, dATP, dTTP, dGTP.

[1] was heat-denatured at 65° C. for 10 minutes, and immediately put on ice.

Then, [1] and [2] were incubated at annealing temperature of 35° C. for one minute, and mixed.

③ Capture of full-length cDNA using streptoavidin beads (a) Selection of full-length cDNA

| | |
|---|---|
| The sample obtained above | 100 µl |
| 10 × RNase I buffer | 50 µl |
| RNase One ™ (Promega) (10 U/µl) | 5 µl |
| DW | 345 µl |
| Total | 500 µl |

The above were incubated at 30° C. for 30 minutes.

(b) Capture of full-length cDNA with streptoavidin beads (1) Binding of Streptoavidin beads (MPG) and Biotinylated RNA-DNA

| | |
|---|---|
| Streptoavidin coated magnetic porous glass (MPG) (CPG, NJ) (1 mg/ml) | 500 µl |
| The sample obtained above | 500 µl |

The above were stirred at room temperature for 30 minutes.

(2) Washing of MPG

[1] Washed with a solution of 50 mM EDTA and 2 M NaCl four times,

[2] a solution of 0.4% SDS and 50 µg/µl yeast tRNA once,

[3] 10 mM NaCl, 0.2 mM EDTA, 10 mM Tris-HCl(pH 7.5), and 20% glycerol once,

[4] an aqueous solution of 50 µg/µl of yeast tRNA once,

[5] RNase H buffer (20 mM Tris-HCl (pH7.5), 10 mM $MgCl_2$, 20 mM KCl, 0.1 mM EDTA, and 0.1 mM DTT) once.

(3) Recover full-length cDNA with RNase H

| | |
|---|---|
| [1] RNase H buffer | 100 µl |
| RNase H | 3 units |

The above were added to the washed MPG and heated at 37° C. for 30 minutes.

| | |
|---|---|
| [2] 10% SDS | 1 µl |
| 0.5M EDTA | 2 µl |

The above were added, heated for 10 minutes at 65° C., and the supernatant was recovered.

(c) cDNA in the supernatant was extracted with phenol/chloroform treatment, and purified by ethanol precipitation.

What is claimed is:

1. A method for making full-length cDNA libraries, which is for making libraries of cDNAs having lengths corresponding to full lengths of mRNAs and comprises the following steps of:
   forming RNA-DNA hybrids by reverse transcription starting from primers using mRNAs as templates, followed by
   chemically binding a tag molecule to a diol structure present in the 5' Cap ($^{7Me}G_{ppp}N$) site of a mRNA which is forming a RNA-DNA hybrid, and separating RNA-DNA hybrids carrying a DNA corresponding to a full-length mRNA from the RNA-DNA hybrids formed above by binding the tag molecule.

2. The method of claim 1, wherein the primer is oligo dT.

3. The method of claim 1, wherein the diol structure present in the 5' Cap site of mRNA is subjected to a ring-open reaction by oxidation with periodic acid to form a dialdehyde and the dialdehyde is reacted with a tag molecule having a hydrazine terminus to form a mRNA binding the tag molecule.

4. The method of claim 3, wherein the tag molecule having a hydrazine terminus is a biotin molecule having a hydrazine terminus (biotin hydrazide) or an avidin or streptavidin molecule having a hydrazine terminus (avidin hydrazide or streptavidin hydrazide).

5. The method of claim 1, wherein the RNA-DNA hybrids binding tag molecules are digested with an RNase capable of cleaving single strand RNA to cleave the single strand parts of the hybrids so that the tag molecules are removed from those hybrids carrying a DNA not corresponding to a full-length mRNA, and then those hybrids carrying a tag molecule and a DNA corresponding to a full-length mRNA are separated.

6. The method of claim 1, wherein the tag molecule is a biotin molecule having a functional group which is capable of biding to a diol structure present in the 5' Cap site of mRNA, and the hybrids carrying a DNA corresponding to a full-length mRNA are separated by utilizing binding properties of avidin or streptavidin fixed on a solid support to the biotin molecule which is the tag molecule of the RNA-DNA hybrid.

7. The method of claim 1, wherein the tag molecule is an avidin or streptavidin molecule having a functional group which is capable of binding to a diol structure present in the 5' Cap site of mRNA, and the hybrids carrying a DNA corresponding to a full-length mRNA are separated by utilizing binding properties of biotin fixed on a solid support to the avidin or streptavidin molecule which is the tag molecule of the RNA-DNA hybrid.

8. A method for making full-length cDNA libraries, which is for making libraries of cDNAs having lengths corresponding to full lengths of mRNAs and comprises the following steps of:
   forming RNA-DNA hybrids by reverse transcription starting from primers using mRNAs as templates, followed by
   binding a biotin molecule to a diol structure present in the 5' Cap ($^{7Me}G_{ppp}N$) site of a MRNA which is forming a RNA-DNA hybrid,
   digesting RNA-DNA hybrids binding biotin molecules with an RNase capable of cleaving single strand RNA to cleave the single strand RNA parts of the hybrids carrying a DNA not corresponding to a full-length mRNA to remove biotin molecules from the hybrids, and
   separating hybrids carrying a DNA corresponding to a full-length mRNA and binding with a biotin molecule by allowing them to react with avidin or streptavidin fixed on a solid support.

9. A method for making full-length cDNA libraries, which is for making libraries of cDNAs having lengths corresponding to full lengths of mRNAs and comprises the following steps of:
   forming RNA-DNA hybrids by reverse transcription starting from primers using mRNAs as templates, followed by
   binding an avidin or streptavidin molecule to a diol structure present in the 5' Cap ($^{7Me}G_{ppp}N$) site of a mRNA which is forming a RNA-DNA hybrid,
   digest in g RNA-DNA hybrids binding avidin or streptavidin molecules with an RNase capable of cleaving single strand RNA to cleave the single strand RNA parts of the hybrids carrying a DNA not corresponding t o a full-length mRNA to remove avidin or streptavidin molecules from the hybrids, and
   separating hybrids carrying a DNA corresponding to a full-length mRNA and binding with an avidin or streptavidin molecule by allowing them to react with biotin fixed on a solid support.

10. The method of claim 8 or 9, wherein the primer is oligo dT.

11. The method of claim 5, wherein the RNase capable of cleaving single strand RNA is ribonuclease I.

12. The method of claim 1, wherein single strand full-length cDNAs are recovered from the separated hybrids having a DNA corresponding to a full-length mRNA.

13. The method of claim 12, wherein the single strand full-length cDNAs are recovered by treating the separated hybrids carrying a DNA corresponding to a full-length mRNA with alkaline phosphatase of tobacco mosaic virus to separate tag molecules from Cap sites.

14. The method of claim 12, wherein the single strand full-length cDNAs are recovered by treating the separated hybrids carrying a DNA corresponding to a full-length mRNA with an RNase to cleave RNA strands of DNA-RNA hybrids.

15. The method of claim 14, wherein the RNase capable of cleaving RNA strands of DNA-RNA hybrids is RNase H.

16. The method of claim 1, wherein second CDNA strands are synthesized by using as templates the recovered full-length cDNA strands, the first single strands and after the second cDNA strands are synthesized, the resulting full-length double stranded cDNAs are cloned.

17. The method of claim 16, wherein the second cDNA strands are synthesized by using as templates cDNA strands obtained by ligating an RNA or DNA oligomer to the 3' end of the first cDNA strand and as primers oligomers complementary to the ligated oligomers.

18. The method of claim 17, wherein the second cDNA strands are synthesized by using as templates cDNAs obtained by ligation of poly G, poly C, poly A or poly T to the 3' end of the first CDNA strands with an enzyme which is capable of synthesizing oligo G, oligo C, oligo T or oligo A at the 3' end and does not require any templates and as primers complementary oligo C, oligo G, oligo T or oligo A.

19. The method of claim 18, wherein the enzyme which is capable of synthesizing oligo G, oligo C, oligo T or oligo A at the 3' end and does not require any templates is a terminal nucleotide transferase.

20. The method of claim 2, wherein the diol structure present in the 5' Cap site of MRNA is subjected to a ring-open reaction by oxidation with periodic acid to form a dialdehyde and the dialdehyde is reacted with a tag molecule having a hydrazine terminus to form a mRNA binding the tag molecule.

21. The method of claim 2, wherein the tag molecule having a hydrazide terminus is a biotin molecule having a hydrazine terminus (biotin hydrazide) or an avidin or streptavidin molecule having a hydrazine terminus (avidin hydrazide or streptavidin hydrazide).

22. The method of claim 3, wherein the tag molecule having a hydrazide terminus is a biotin molecule having a hydrazine terminus (biotin hydrazide) or an avidin or streptavidin molecule having a hydrazine terminus (avidin hydrazide or streptavidin hydrazide).

23. The method of claim 2 b wherein the tag molecule is a biotin molecule having a functional group which is capable of binding to a diol structure present in the 5' Cap ste of mRNA, and the hybrids carrying a DNA corresponding to a full-length MRNA are separated by utilizing binding properties of avidin or streptavidin fixed on a solid support to the biotin molecule which is the tag molecule of the RNA-DNA hybrid.

24. The method of claim 2, wherein the tag molecule is an avidin or streptavidin molecule having a functional group which is capable of binding to a diol structure present in the 5' Cap ste of mRNA, and the hybrids carrying a DNA corresponding to a full-length mRNA are separated by utilizing binding properties of biotin fixed on a solid support to the avidin or streptavidin molecule which is the tag molecule of the RNA-DNA hybrid.

25. The method of claim 9, wherein the primer is oligo dT.

26. The method of claim 8, wherein the RNase capable of cleaving single strand RNA is ribonuclease I.

27. The method of claim 9, wherein the RNase capable of cleaving single strand RNA is ribonuclease I.

28. The method of claim 8, wherein the primer is oligo dT, and further wherein the RNase capable of cleaving single strand RNA is ribonuclease I.

* * * * *